United States Patent [19]

Chan

[11] Patent Number: 5,851,438
[45] Date of Patent: Dec. 22, 1998

[54] THICK FILM COMPOSITIONS FOR MAKING MEDICAL ELECTRODES

[75] Inventor: Man-Sheung Chan, Chapel Hill, N.C.

[73] Assignee: E. I. du Pont de Nemours and Company, Wilmington, Del.

[21] Appl. No.: 921,183

[22] Filed: Aug. 29, 1997

[51] Int. Cl.⁶ ............................... H01B 1/22; H01B 1/24
[52] U.S. Cl. ................. 252/514; 252/511; 252/520.3
[58] Field of Search ..................... 252/511, 514, 252/520.3; 106/1.14, 1.19; 524/439

[56] References Cited

U.S. PATENT DOCUMENTS

| | | | |
|---|---|---|---|
| 3,662,745 | 5/1972 | Cosentino | 128/2 E |
| 4,371,459 | 2/1983 | Nazarenko | 252/514 |
| 4,747,819 | 5/1988 | Phipps et al. | 604/20 |
| 4,752,285 | 6/1988 | Petelenz et al. | 604/20 |
| 4,877,512 | 10/1989 | Bowns eet al. | 204/435 |
| 5,051,208 | 9/1991 | Bowns et al. | 252/511 |
| 5,147,297 | 9/1992 | Myers et al. | 604/20 |
| 5,389,403 | 2/1995 | Buckley et al. | 252/514 |
| 5,565,143 | 10/1996 | Chan | 252/514 |

OTHER PUBLICATIONS

P. Glickfield et al., Pharmaceutical Research,*Noninvasive Sampling of Biological Fluids*, 6(11), 988–990, 1989.

O. Wong, Iontophoresis: Fundamentals, *CygnusTherapeutic Systems, Redwood City, CA*. No. Pub. Info.

*Primary Examiner*—Mark Kopec

[57] ABSTRACT

The invention is directed to a conductive composition for iontophoretic electrodes comprising, based on solids: (a) 20–90% wt finely divided particles of silver, carbon, graphite and mixtures thereof; (b) 0–75% wt. finely divided particles of silver chloride; (c) 0.25–10% wt. hydrophilic polymer; and (d) 2–15% wt. hydrophobic thermoplastic polymer having a glass transition temperature (Tg)>40° C. The invention is also directed to compositions wherein the binder comprises 5–15% wt. copolymer of hydrophilic and hydrophobic monomers.

10 Claims, No Drawings

THICK FILM COMPOSITIONS FOR MAKING MEDICAL ELECTRODES

FIELD OF THE INVENTION

This invention relates to an improvement in conductive polymer thick film compositions for making medical electrodes used in iontophoretic transdermal drug delivery devices.

BACKGROUND OF THE INVENTION

Medical electrodes are commonly used in two broad applications, namely, iontophoretic transdermal drug delivery and medical diagnostics by electrochemical methods. In the area of iontophoretic transdermal drug delivery, electrodes are the key elements in an electrochemical device that drives charged drug ions through the skin by an electrical current. "Iontophoresis: Fundamentals" by O. Wong, Cygnus Therapeutic Systems, Redwood City, Calif. provides an overview of iontophoretic transdermal drug delivery technology, and "Noninvasive Sampling of Biological Fluids by Iontophoresis" by P. Glickfeld et al., Pharmaceutical Research, Vol. 6, No. 11. 1989, describes the use of iontophoretic techniques to extract biological molecules from a human body for medical diagnosis. The content of the articles are incorporated herein. In the area of medical diagnostics, conventional Ag/AgCl electrodes serve as transducers that convert electrochemical signals derived from the human body to electronic signals which measures/monitors body or organ functions by conventional electronic instruments, such as electrocardiograph (EKG), electroencephalograph (EEG) and blood sensors. There is a significant difference between conventional Ag/AgCl electrodes and iontophoretic electrodes. Iontophoretic electrodes undergo extensive compositional changes within the electrodes after use; while there is little change in conventional Ag/AgCl electrodes after use. Silver and silver/silver chloride polymer thick film (PTF) printing inks for iontophoretic electrodes having high electrode capacity are needed to sustain long-duration (>24 hours) drug delivery. An iontophoretic drug delivery device comprises an electrochemical cell consisting of a donor electrode coated with a drug/hydrogel mixture, a counter electrode coated with hydrogel, and an electrical current supply. The electrodes are adhered to a patient's skin and then a low electric current, typically <0.2 miliampere/cm2 ($mA/cm^2$) in current density, is applied to the device. Charged drug species are driven through the skin by the electric field between the two electrodes. Accompanying the electric current, an oxidation reaction at the anode and a reduction reaction at the cathode take place to maintain the electrons/ions balance within the electrochemical cell. In the case of Ag/AgCl PTF electrodes, Ag is oxidized to AgCl at the anode and AgCl is reduced to Ag at the cathode. As Ag and AgCl are depleted in the electrodes, the respective electrode potentials increase to high values which may lead to harmful side reactions that render these electrodes unsuitable for further iontophoretic drug delivery and limits the full utilization of Ag in the anode. Investigations were conducted to look into the causes of deficiencies in the presently known iontophoretic electrode materials, such as a silver foil or polymer silver/silver chloride composites. When tested in an electrochemical cell, these electrodes were found to quickly form a thin layer of silver chloride as a result of electrochemical oxidation of silver on the anode surface when an electric current passed through the cell. This insulating silver chloride layer leads to increased electrode potential and also hinders further electrochemical oxidation of silver, and eventually high electrode potential renders the device unusable for drug delivery when harmful side reactions occurs. This problem of Ag-to-AgCl conversion limited at the electrode surface is due to the inability of the chloride ion to penetrate inside the anode. A hydrophobic electrode surface and a hydrophobic polymer binder matrix of a polymer thick film (PTF) electrode coating are the two major barriers that hinder chloride ion transport into the anode for sustaining the Ag-to-AgCl conversion throughout the thickness of the electrode PTF coating.

Therefore choosing the proper anode and cathode materials is critical to the success of achieving the best efficiency coupled with low cost for an iontophoretic device. U.S. Pat. No. 4,752,285 to Petelenz et al. and U.S. Pat. No. 4,747,819 to Phills et al. disclose iontophoretic devices with silver or lead metal anodes and silver chloride cathodes. U.S. Pat. No. 5,147,297 to Myers et al. discloses an iontophoretic device using electrodes composed of hydrophobic polymers, conductive fillers and chemical species, such as silver and silver chloride, capable of undergoing oxidation-reduction reactions. However, these electrodes suffer from several deficiencies, such as: (a) difficult to assemble into patches that can conform to the contour of human body, and (b) limited capacities to sustain the electric current for long drug delivery duration due to the limited capacity of anode materials. U.S. Pat. No. 3,662,745 to Cosentino discloses EKG/EEG type of electrodes prepared by coating a Ag/AgCl paste containing hydrophobic and hydrophilic polymers, alumina powder, and silver and silver chloride powders onto an electrically conductive substrate to improve electrode sensitivity for electrochemical measurements. These electrodes suffer from low conductivity and low capacities for sustaining an electric current which is needed for a long duration in iontophoretic drug delivery systems. U.S. Pat. No. 4,371,459 to Nazarenko et al. and U.S. Pat. Nos. 4,877,512 and 5,051,208 to Bowns et al. discloses silver and silver/silver chloride conductive PTF compositions containing hydrophobic polymers. These Ag and Ag/AgCl conductive compositions were developed for flexible circuits and EKG, EEG electrode applications, and were found to suffer from deficiencies described above when used as electrodes for an iontophoretic device. An attractive approach to overcome the deficiencies mentioned above is to print electrodes with conductive polymer thick film (PTF) materials on a plastic film substrate to make flexible electrodes that can then be easily assembled into convenient transdermal patches. The present invention provides conductive Ag or Ag/AgCl PTF compositions for medical electrodes which meet this need and the need for long-term iontophoretic drug delivery. In addition, the present invention overcomes the deficiencies in existing iontophoretic drug delivery systems by: (a) efficiently utilizing the oxidation-reduction species to achieve low cost, (b) obtaining high capacity for long-duration drug delivery, (c) exhibiting screen printability, and (d) displaying good adhesion to plastic flexible film substrates.

SUMMARY OF INVENTION

The invention is directed to a conductive composition for iontophoretic electrodes comprising, based on solids:
(a) 20–90% wt finely divided particles of silver, carbon, graphite and mixtures thereof;
(b) 0–75% wt. finely divided particles of silver chloride;
(c) 0.25–10% wt. hydrophilic polymer; and
(d) 2–15% wt. hydrophobic thermoplastic polymer having a glass transition temperature $(T_g) > 40°$ C.

The invention is also directed to compositions wherein the binder is 5–15% wt. a copolymer of hydrophilic and hydrophobic monomers.

DETAIL DESCRIPTION OF THE INVENTION

Polymer Binder

Several approaches can be used to make a binder matrix hydrophilic, or partially hydrophilic. They include (a) a hydrophilic polymer binder, (b) a binder blend of hydrophilic and hydrophobic polymers, (c) a binder being a copolymer of hydrophobic and hydrophilic monomers. However, a PTF coating with a straight hydrophilic polymer as the binder has the drawback of low coating cohesive strength and low adhesion to plastic film substrates when exposed to water, and therefore is not suitable for uses as iontophoretic electrodes which are always in contact with saline water. It was found the use of a partially hydrophilic copolymer or a polymer blend as the binder for a PTF Ag/AgCl electrode composition provides good balance of ion transport, high electrode capacity, good cohesive coating strength, good adhesion to a suitable substrate, such as a poly(ethylene terephthalate) (PET) substrate. In a PTF coating with a binder of a hydrophobic/hydrophilic polymer blend, it is the hydrophobic polymer that provides the good coating cohesive strength and strong adhesion to plastic film substrates even when exposed to saline water. Suitable hydrophobic binder additions are thermoplastic polymers with glass transition temperatures of $(T_g) > 40°$ C. so that coatings with good flexibility and good coating hardness at ambient temperature can be maintained. Suitable thermoplastic polymers are from the group of PET resins such as VITEL® resins from Goodyear Tire & Rubber Co., poly(hydroxyether) such as UCAR® phenoxy resins available from Union Carbide Co., acrylic resins such as ELVACITE® resins available from ICI Inc., vinyl chloride resin, poly(vinylidene chloride-acrylonitrile) such as SARAN® available from Dow Chemicals Inc., poly(styrene-acrylonitrile) such as TYRIL® resins available from Dow Chemicals Inc., poly(styrene-butadiene-acrylonitrile) such as LUSTRAN® ABS resins from available Monsanto Inc. Hydrophilic polymers suitable for the present invention are polymers that are water soluble or substantially soluble in water. They are polymers chosen from the group of poly(vinyl pyrrolidone) and poly(vinyl pyrrolidone-vinyl acetate), poly(acrylamide), poly(vinyl methyl ether), poly(ethylene oxide), poly(vinyl alcohol), poly(hydroxyalkyl methacrylate).

To make a suitable polymer blend, the hydrophilic and hydrophobic polymer pair have to be compatible with each other to form a uniform polymer mixture in a desirable ratio. The polymer blend has to be soluble in a desirable solvent suitable for making PTF materials. To achieve the desirable coating properties and good ion transport characteristics, the suitable ratio by weight of hydrophilic polymer to hydrophobic polymer is in the range of 5/95 to 60/40, preferably in the range of 25/75 to 35/65. Too much of hydrophilic polymer in the polymer binder tends to weaken the coating cohesive strength and adhesion to plastic film substrates. Too little hydrophilic polymer in the polymer binder matrix tends to limit ion transport and thus electrode capacities. To achieve good balance of coating strength and high electrode capacity, 30–50% by volume of polymer in the PTF dry coating is needed. Based on solids, 0.25–10% wt. hydrophilic polymer and 2–15% wt. hydrophobic thermoplastic polymer is used in the composition.

Partially hydrophilic polymer binder suitable for the present invention can also be a copolymer of a hydrophilic monomer and a hydrophobic monomer. A suitable copolymer can be chosen from the group of poly(vinyl chloride-hydroxypropyl methacrylate) and poly(vinyl chloride-vinyl alcohol) such as UCAR® vinyl resins from Union Carbide Inc., poly(styrene-vinyl pyrrolidone), poly(vinyl pyrrolidone vinyl acetate) from International Specialty Products Inc., acrylic polymers containing water-soluble monomer such as hydroxyethyl methacrylate, acrylamide and methacrylamide. Based on solids, 5–15% wt. of copolymer of hydrophilic and hydrophobic monomers are utilized in the present invention.

Organic Vehicle

The main purpose of the vehicle is to serve as a medium for dispersion of the polymer binder and electrically conductive particles, collectively called solids. Thus, the vehicle must first be a good solvent for the polymer so that a stable uniform dispersion of inorganic fillers in the polymer solution can be made. Secondly, the rheological properties of the vehicle must be such that they lend good application properties to the composition. Thirdly, the vehicle can be printed and then dried by a conventional screen printing process.

Since hydrophilic polymers and hydrophobic polymers are not normally soluble in the same type solvent, a solvent mixture is typically used for this type of polymer blend. Typically a suitable solvent mixture is chosen from the group of dibasic esters, such as DBE® solvents from DuPont, DE, ethylene or propylene glycol monoalkyl ethers and their acetates, such as DOWANOL® solvents from Dow Chemicals Inc., MI and ARCOSOLV® solvents from Arco Chemicals Inc. PA., ketones, such as acetophenone, benzoacetone and alkyl ketones, n-methyl pyrrolidone, butyrolactone and aromatic solvents. When used in a fast drying coating process, a mixture of solvent chosen from the group of ethanol or isopropanol, methyl ethyl ketone or methyl isobutyl ketone, and propyl or butyl acetate solvents is suitable. These organic solvents are also suitable vehicles for copolymers of hydrophilic monomers and hydrophobic monomers.

The ratio of vehicle to solids in the dispersions can vary considerably and depends upon the manner in which the dispersion is to be applied and the kind of vehicle used. Normally to achieve good coverage the dispersions will contain complementally, 60–90% solids and 40–10% vehicle. The compositions of the present invention may, of course, be modified by the addition of other materials which do not affect its beneficial characteristics. Such formulation is well within the skill of the art.

The pastes are conveniently prepared on a three-roll mill. The viscosity of the pastes is typically 10–50 Pa.S (Brookfield RVT, 10 rpm, # 5 spindle) at shear rate of 0.4/s when measured on a Brookfield HBT viscometer. The amount of vehicle utilized is determined by the final desired formulation viscosity.

Electrically conductive particles

In a Ag or Ag/AgCl iontophoretic anode, silver particles serve as the oxidizable species and the conductive filler. The silver particles used in the anode of the present invention are finely divided particles with a preferable particle size within the range of 1 micron to 25 microns. Very fine silver powder is not efficient in forming a conductive network for electron conduction and also leads to undesirably high PTF paste viscosity. On the other hand, large silver flakes leads to problems of printing. The loading of silver particles in the PTF coating determines the conductivity and the anode capacity. Typically, 20 percent or more by volume of silver particles are needed to form a conductive network. Typically 20–90% wt. is used in the composition with the preferred silver powder content in the range of 25–95% by weight in a Ag or Ag/AgCl PTF coating. The typical ratio of Ag/AgCl is in the range of 100/0 to 80/20 by weight for anode coating.

In a Ag/AgCl iontophoretic cathode, silver chloride serves as the reducible species to sustain the iontophoretic current. The silver chloride component is in powder form with a particle size in the range of 0.1 micron to 15 microns. Silver chloride powder, such as those commercially available from Colonial Metal Inc., DE, typically comes in agglomerated form and need to be dispersed in a PTF paste by milling processes. The amount of silver chloride in a Ag/AgCl electrode coating has to be balanced with the amount of polymer binder and conductive particles, such as Ag and graphite particles. Typically 0–75% wt. is used in the composition with the preferred amount of AgCl powder in the range of 25–75 percent by weight of solids. The typical silver to silver chloride ratio is in the range of 15/85 to 35/65 by weight for a conductive cathode coating.

In some iontophoretic drug delivery devices, the electric current can be reversed alternately so that drug can delivered by both the working electrode and the counter electrode. Each electrode functions alternately as anode and cathode when each time the current polarity changes. An Ag/AgCl paste with equal anode and cathode capacity is needed to meet this requirement. Typically, a paste with a silver to silver chloride weight ratio in the range of 70/30 to 65/35 provides electrodes suitable for a reversible iontophoretic drug delivery device.

Graphite and conductive carbon particles can be used to replace or partially replace silver particles as the conductive filler in a Ag/AgCl composition or may partially replace Ag in a Ag composition. To form a carbon conductive network, the carbon-graphite need be >40% by volume of the solids with the remaining volume taken up by the inorganic Ag or AgCl and polymer binder. The preferred amount of conductive carbon and graphite is 30–40% by weight of solids.

Silver flakes or powders often come with up to 0.5% adsorbed surfactants to stabilize the silver particles in liquid dispersions. However, excessive surfactant can lead to a hydrophobic coating surface due to surfactant migrating to the air surface during drying of a thick Ag/AgCl coating. A hydrophobic surface is a significant barrier for chloride ion transport and thus lowers the efficiency of the Ag-to-AgCl conversion. It is preferred that surfactant level be well below 0.2% by weight and a suitable solvent be used to minimize the formation of a hydrophobic electrode surface caused by surfactant migration during drying. Suitable surfactants are chosen from the group of anionic surfactants such as sodium stearate, sodium oleate, long chain alkyl phosphate.

The inorganic particles are mixed with an essentially inert liquid medium (vehicle) which a solution of polymer binder dissolved in the desired solvent by mechanical mixing using a planetary mixer, then dispersed on a three roll mill to form a paste-like composition having suitable consistency and rheology for screen printing. The latter is printed as a "thick film" on plastic film substrates such as polyester film in the conventional manner.

The ratio of vehicle to solids in the dispersions can vary considerably and depends upon the manner in which the dispersion is to be applied and the kind of vehicle used. Normally to achieve good coverage, the dispersions will contain complementarily 60–90% solids and 40–10% vehicle, as described above. The compositions of the present invention may, of course, be modified by the addition of other materials which do not affect its beneficial characteristics. Such formulations is well within the skill of the art. The amount of vehicle is determined by the final desired formulation viscosity.

The compositions of this invention can be printed onto plastic film substrates either by using an automatic printer or a hand printer in the conventional manner. Preferably, automatic screen stenciling techniques are employed, using a 200– or lower mesh screen.

Formulation and Application

In the preparation of the compositions of the present invention, the particulate inorganic solids are mixed with the organic medium and dispersed with suitable equipment, such as three-roll mill, to form a suspension, resulting in a composition for which the viscosity will be in the range of about 15–50 pascal-seconds (Brookfield RVT, 10 rpm, #5 spindle).

In the examples which follow, the formulation was carried out in the following manner:

The ingredients of the paste are weighed together in a container. The components are then vigorously mixed to form a uniform blend; then the blend is passed through dispersing equipment, such as a three-roll mill, to achieve a good dispersion of particles. A Hegman gauge is used to determine the state of dispersion of the particles in the paste. This instrument consists of a channel in a block of steel that is 25 $\mu$m deep (1 mil) on one end and ramps up to zero depth at the other end. A blade is used to draw down paste along the length of the channel. Scratches appear in the channel where the agglomerates' diameter is greater than the channel depth. A satisfactory dispersion will give a fourth scratch point of 10–18 $\mu$m typically. The point at which half of the channel is uncovered with a well dispersed paste is between 3 and 8 $\mu$m typically. Fourth scratch measurement of >20 $\mu$m and "half-channel" measurements of >10 $\mu$m indicate a poorly dispersed suspension.

The compositions are then applied to a substrate, such as a PET substrate, usually by the process of screen printing, to a dry thickness of 100 microns depending on the drug delivery duration required". The compositions of this invention can be printed onto the substrates either by using an automatic printer or a hand printer in the conventional manner, preferably automatic screen printing techniques are employed using a 60– to 165-mesh screen. The printed pattern is then dried at about 120° C. for about 5–15 minutes.

The present invention will be described in further detail by giving practical examples. The scope of the present invention, however, is not limited in any way by these practical examples.

EXAMPLE 1

This example demonstrate the preparation of a Ag PTF composition containing a hydrophobic/hydrophilic polymer blend suitable for use in making iontophoretic anode. Acrylic resin and PVP-VA resin were dissolved in dipropylene glycol methyl ether. Silver flake and silver powder were added to the polymer solution with mixing and then milled on a 3-roll mill to a fineness reading of <5 micron as detailed above. The resultant paste has a viscosity of "20–30Pa.S"

| Ingredient | Percent by Weight |
| --- | --- |
| Acrylic resin (1) | 4.0 |
| PVP-VA resin (2) | 1.7 |
| Dipropylene glycol methyl ether | 10.5 |
| Silver flake | 20.7 |
| silver powder | 62.1 |
| | 100.0 |

(1) Elvacite 2016 resin from ICI, MO
(2) PVP-VA S-630 resin from International Specialty Products, NJ

EXAMPLE 2

This example demonstrates the preparation of a Ag/AgCl ink containing an acrylic/PVP-VA polymer blend suitable for use as an iontophoretic cathode. Paste sample was prepared in the same way as Example 1.

| Ingredients | Percent by Weight |
| --- | --- |
| PVP-VA resin (2) | 2.5 |
| Acrylic resin (1) | 5.9 |
| Dipropylene glycol methyl ether | 12.2 |
| Aromatic 150 | 3.0 |
| Silver flake | 24.8 |
| Silver chloride (3) | 51.6 |
| | 100.0 |

(3) 325 mesh AgCl powder from Colonial Metals Inc., DE

EXAMPLE 3

This example demonstrates the preparation of a Ag/AgCl paste with a hydrophilic/hydrophobic polymer blend suitable for use in an iontophoretic anode. Acrylic resin and PVP-VA resin were dissolved in diethyl oxalate and then Ag flakes and AgCl powder were added with mixing. The paste mixture was then milled on a 3-roll mill to a fineness reading of <5 micron. The resultant Ag paste has a viscosity of 25–30 Pa.S.

| Ingredient | Percent by Weight |
| --- | --- |
| Acrylic resin (1) | 4.17 |
| PVP-VA resin (2) | 1.78 |
| Diethyl oxalate | 11.05 |
| Silver flake | 78.87 |
| Silver chloride | 4.13 |
| | 100.0 |

EXAMPLE 4

This example shows a Ag PTF composition for iontophoretic anode having a partially hydrophilic copolymer as the polymeric binder. Paste sample was prepared in the same way as Example 1.

| Ingredient | Percent by Weight |
| --- | --- |
| PVP-VA E335 resin (4) | 6.1 |
| Diethyl oxalate | 14.1 |
| Silver flake | 79.8 |
| | 100.0 |

(4) PVP-VA E335 from International Specialty Products, NJ

EXAMPLE 5

This example shows a Ag PTF composition having a copolymer of hydrophilic acrylic monomer and hydrophobic vinyl monomer as the polymeric binder. Paste sample was prepared in the same way as Example 1.

| Ingredient | Percent by Weight |
| --- | --- |
| Poly(vinyl chloride-hydroxypropyl methacrylate) resin (5) | 6.7 |
| N-methyl pyrrolidone | 7.2 |
| Aromatic 150 | 12.0 |
| Silver flake | 18.5 |
| Silver powder | 55.6 |
| | 100.0 |

(5) UCAR* vinyl resin VAGF resin from Union Carbide, Danbury CT

EXAMPLE 6

This example shows a Ag/AgCl PTF composition for iontophoretic cathode printed on a conductive substrate. Paste sample was prepared in the same way as Example 2.

| Ingredient | Percent by Weight |
| --- | --- |
| PVP-VA resin (2) | 2.6 |
| Acrylic resin (1) | 6.0 |
| Dipropylene glycol methyl ether | 14.0 |
| Aromatic 150 | 3.5 |
| Silver chloride (3) | 59.1 |
| Silver flake | 14.8 |
| | 100.0 |

EXAMPLE 7

This example demonstrate a Ag/AgCl composition suitable for both cathode and anode in a reversible iontophoretic drug delivery device. Ink sample was prepared using the same procedure as Example 1.

| Ingredient | Percent by Weight |
| --- | --- |
| Acrylic resin (1) | 5.13 |
| PVP-VA resin (2) | 2.2 |
| Aromatic 150 | 2.2 |
| Dipropylene glycol methyl ether | 8.8 |
| Silver flake | 13.27 |
| Silver powder | 39.8 |
| Silver chloride | 28.6 |
| | 100.0 |

EXAMPLE 8

This example demonstrates the preparation of a conductive carbon and AgCl composition suitable for iontophoretic cathode.

| Ingredient | Weight percent |
| --- | --- |
| Phenoxy resin (6) | 8.1 |
| PVP-VA resin (2) | 2.7 |
| Dipropylene glycol methyl ether | 22.4 |
| Aromatic 150 | 7.8 |
| Butyrolactone | 13.0 |
| Silver chloride | 25.6 |
| Conductive carbon (7) | 10.2 |
| Graphite (8) | 10.2 |
| Sodium stearate | 0.2 |
| | 100.0 |

(6) Phenoxy PKH from Union Carbide, CT
(7) VULCAN XC-72R from Carbot, MA
(8) HPN-10 graphite from Dixon Ticonderoga, NJ

EXAMPLE 9

A silver and carbon paste was prepared for use as an iontophoretic anode.

| Ingredient | Weight percent |
| --- | --- |
| Acrylic resin (1) | 6.6 |
| PVP-VA resin (2) | 2.8 |
| Dipropylene glycol methyl ether | 33.1 |
| Conductive carbon (7) | 6.3 |
| Graphite (8) | 14.8 |
| Silver flake | 10.2 |
| Silver powder | 26.2 |
| | 100.0 |

EXAMPLE 10 COMPARATIVE

A silver PTF paste containing a hydrophobic phenoxy resin was prepared in the same manner as in Example 1 with the composition shown below. The ink sample was printed and tested as an iontophoretic anode.

| Ingredient | Percent by Weight |
| --- | --- |
| Phenoxy resin (6) | 5.9 |
| Dipropylene glycol methyl ether | 24.1 |
| Silver flake | 70.0 |
| | 100.0 |

EXAMPLE 11 COMPARATIVE

A PTF paste containing a silver/silver chloride and hydrophobic PET resin was prepared in the same way as Example 1 and then tested as an iontophoretic anode.

| Ingredient | Percent by Weight |
| --- | --- |
| Acrylic resin (9) | 9.2 |
| Propylene glycol methyl acetate | 8.9 |
| Ethylene glycol butyl acetate | 11.9 |
| Silver flake | 70.0 |
| | 100.0 |

(9) Acryloid A-11 from Rohm-Haas, PA

ELECTRODE TESTINGS

A Ag or Ag/AgCl PTF composition is typically screen printed on a PET film substrate to a targeted coat weight using wire mesh screen of 165-60 mesh. For Example 6, the Ag/AgCl coating was printed on a conductive carbon coating on a PET substrate. The dried coating was then tested as an anode or a cathode in an electrochemical test cell. The test cell consists of a 0.9% NaCl solution (saline water), a test electrode with 1 $cm^2$ submerged in the saline water and a counter electrode having a known electrode capacity of >100 miliampere.minutes/$cm^2$ (mA.min./cm2) with 6 $cm^2$ submerged in the saline water. A power supply and a chart recorder were connected to the two electrodes. During testing, a constant current, typically at 0.5 mA, was applied to the two electrodes, and the voltage across the two electrodes was recorded vs time on a chart recorder. The test was stopped when the voltage reached one volt at which electrolysis of water became significant rendering further iontophoretic drug delivery undesirable. The electrode capacity of a test electrode, measured in unit of mA.min./$cm^2$, is calculated by multiplying the recorded time in minute by 0.5 mA/cm2. Typical capacity for Ag and AgCl PTF examples described above are listed below. For comparison, a typical iontophoretic device operating at a current density of 0.1 mA/cm2 requires a electrode capacity of 144 mA.min./cm2 for both cathode and anode to sustain a 24-hour drug delivery.

| Example | Coat Weight (gm/$cm^2$) | Electrode Capacity (mA.min./$cm^2$) | |
| --- | --- | --- | --- |
| | | Anode | Cathode |
| 1 | 59.8 | 560 | — |
| 2 | 23.7 | — | 222 |
| 3 | 31.4 | 170 | — |
| 4 | 10.3 | 70 | — |
| 5 | 19.2 | 53 | — |
| 6 | 7.1 | — | 58 |
| 7 | 30.8 | 188 | 230 |
| 8 | 7.9 | — | 33 |
| 9 | 13 | 70 | — |
| 10 | 16.8 | 4 | — |
| 11 | 21.7 | 3 | — |

What is claimed is:

1. A conductive composition for iontophoretic electrodes comprising, based on solids:
   (a) 20–90% wt. of silver particles;
   (b) 0–75% wt. of silver chloride particles;
   (c) 0.25–10% wt. hydrophilic polymer; and
   (d) 2–15% wt. hydrophobic thermoplastic polymer having a Tg above 40° C. said conductive composition further comprising a vehicle consisting of organic solvent or organic solvent mixtures.

2. The composition of claim 1 wherein the hydrophilic polymer is selected from the group consisting of poly (vinylpyrrolidone), poly(vinylpyrrolidone-vinyl acetate), poly(vinyl methyl ether), poly(ethylene oxide), poly(vinyl alcohol), poly(acrylamide), and poly(hydroxyalkyl methacrylate).

3. The composition of claim 1 wherein the hydrophobic polymer is selected from the group consisting of acrylic polymer, polyhydroxyether, poly(styrene-acrylonitrile), poly(vinylidene chloride-acrylonitrile), polyester, poly (acrylonitrile-butadiene-styrene).

4. The composition in claim 1 wherein the silver particles are in the range of 1–25 microns.

5. The composition in claim 1 wherein the silver chloride particles are in the range of 0.1–15 microns.

6. The composition in claim 1 further comprising conductive fillers selective from the group consisting of carbon and graphite.

7. The composition in claim 1 wherein the organic vehicle is selected from the group consisting of alkyl ketones, aromatic ketones, glycol alkyl ethers and their acetates, dibasic esters, n-methylpyrrolidone, butyrolactone, and aromatic solvents.

8. The composition of claim 1 wherein silver to silver chloride ratio is in the range of 100/0 to 80/20 by weight for iontophoretic anode.

9. The composition of claim 1 wherein silver to silver chloride ratio is in the range of 15/85 to 35/65 by weight for iontophoretic cathode.

10. The composition of claim 1 wherein the silver to silver chloride ratio by weight is in the range of 70/30 to 65/35.

* * * * *